United States Patent [19]
Schroeck

[11] 3,960,918
[45] June 1, 1976

[54] PREPARATION OF ESTERS OF AMIDOALKANESULFONIC ACIDS

[75] Inventor: Calvin William Schroeck, Eastlake, Ohio

[73] Assignee: The Lubrizol Corporation, Cleveland, Ohio

[22] Filed: Apr. 15, 1974

[21] Appl. No.: 461,205

Related U.S. Application Data

[63] Continuation-in-part of Ser. No. 373,698, June 26, 1973, abandoned.

[52] U.S. Cl.......................... 260/456 A; 260/513 N
[51] Int. Cl.$^2$....................................... C07C 143/68
[58] Field of Search..................... 260/456 A, 513 N

[56] References Cited
UNITED STATES PATENTS

| | | | |
|---|---|---|---|
| 3,235,549 | 2/1966 | Broussalian.................... | 260/513 N |
| 3,274,231 | 9/1966 | Kobayashi..................... | 260/513 N |
| 3,544,597 | 12/1970 | Killam............................ | 260/513 N |

FOREIGN PATENTS OR APPLICATIONS

| | | | |
|---|---|---|---|
| 1,090,779 | 11/1967 | United Kingdom............ | 260/513 N |

Primary Examiner—James O. Thomas, Jr.
Assistant Examiner—Nicky Chan
Attorney, Agent, or Firm—James W. Adams, Jr.; William H. Pittman

[57] ABSTRACT

Esters of amidoalkanesulfonic acids are prepared by bringing the acid into contact with sulfur trioxide and subsequently adding an organic hydroxy compound which may be an alcohol or phenol and is preferably an alcohol. The sulfur trioxide is ordinarily furnished by fuming sulfuric acid (oleum). In a preferred embodiment, the amidoalkanesulfonic acid is prepared in situ from a nitrile, an olefin and fuming sulfuric acid, and the fuming sulfuric acid used in the preparation of the acid also furnishes the sulfur trioxide for the ester formation. The esters derived from unsaturated amides are useful monomers, especially for copolymerization with acrylic compounds to produce polymers of improved dyeability.

13 Claims, No Drawings

PREPARATION OF ESTERS OF AMIDOALKANESULFONIC ACIDS

This application is a continuation-in-part of copending application Ser. No. 373,698, filed June 26, 1973, now abandoned.

This invention relates to new methods of preparing compositions of matter, and particularly for preparing esters of amidoalkanesulfonic acids. Still more particularly, it relates to a method for the preparation of such esters which comprises bringing into contact an amidoalkanesulfonic acid and sulfur trioxide, and subsequently contacting the reaction mass thus obtained with an organic hydroxy compound of the formula ROH, wherein R is a hydrocarbon or substituted hydrocarbon radical.

The most usual method for the preparation of sulfonic acid esters is to convert the acid to the corresponding sulfonyl chloride and to react said sulfonyl chloride with an alcohol. At best, this method is cumbersome and somewhat hazardous since the reagents used to convert the acid to its chloride are difficult and relatively dangerous to handle. In the case of amidoalkanesulfonic acids, the sulfonyl chloride has hitherto been incapable of preparation and so the method is not available. Direct esterification reagents such as diazomethane are also undesirable since their use is not entirely safe, and the direct preparation of a sulfonic ester by reaction of the sulfonic acid with the alcohol has generally not been successful.

A principal object of this invention, therefore, is to provide a new method for the preparation of esters of amidoalkanesulfonic acids.

A further object is to provide a convenient method for preparing such esters in high yields.

Still another object is to provide a method for the preparation of amidoalkanesulfonic acid esters which involves the use of readily available reagents capable of safe use.

Other objects will in part be obvious and will in part appear hereinafter.

The present invention is based on the discovery that the direct preparation of esters of amidoalkanesulfonic acids, by the reaction of an organic hydroxy compound with the free acid, may be conveniently carried out in the presence of sulfur trioxide. As pointed out hereinafter, the sulfur trioxide may be used in any of several forms.

The amidoalkanesulfonic acids which are converted to esters according to this invention are known compounds. Their preparation is described in a number of patents including U.S. Pat. No. 3,544,597. According to the method therein described, a nitrile is reacted with an olefin in the presence of fuming sulfuric acid and the amidoalkanesulfonic acid precipitates directly from the reaction mixture. The present invention contemplates the use of such amidoalkanesulfonic acids, as isolated from the mixture disclosed in the above-noted patent. It is also, however, within the scope of this invention to prepare the amidoalkanesulfonic acid in situ from the nitrile, olefin and fuming sulfuric acid, and as pointed out hereinafter, the same fuming sulfuric acid is useful as a source of sulfur trioxide for the purposes of this invention.

The nitrile used to prepare the amidoalkanesulfonic acid is preferably a hydrocarbon nitrile (that is, a nitrile wherein the CN group or groups are attached to a hydrocarbon radical) and still more preferably an alkyl or alkenyl nitrile.

The term "hydrocarbon radical," as used herein, includes aliphatic, alicyclic and aromatic (including aliphatic- and alicyclic-substituted aromatic and aromatic-substituted aliphatic and alicyclic) radicals.

The following are illustrative of hydrocarbon radicals within the scope of this invention. Where a named radical has several isomeric forms (e.g., butyl), all such forms are included.

| | |
|---|---|
| Methyl | Tolyl |
| Ethyl | Xylyl |
| Propyl | Benzyl |
| Butyl | Cyclohexyl |
| Hexyl | Cyclopentyl |
| Octyl | Methylcyclopentyl |
| Decyl | Cyclopentadienyl |
| Vinyl | Vinylphenyl |
| Allyl | Isopropenylphenyl |
| Ethynyl | Cinnamyl |
| Propargyl | Naphthyl |
| Phenyl | |
| $-C_6H_3(C_2H_5)_2$ | |
| $-C_6H_4(CH_2)_{11}CH_3$ | |
| $-CH_2CH(CH_3)-\text{naphthyl}$ | |
| $-CH_2-\text{cyclohexyl}-CH_3$ | |

Many obvious variations of these radicals will be apparent to those skilled in the art and are included within the scope of the invention.

Substituted hydrocarbon, alkyl, alkenyl, etc., radicals are considered fully equivalent to the hydrocarbon, alkyl, alkenyl, etc., radicals for the purpose of this invention. By "substituted" is meant radicals containing substituents which do not alter significantly the character or reactivity of the radical. Examples are:
  Halide (fluoride, chloride, bromide, iodide)
  Ether (especially lower alkoxy)
  Carboxy
  Ester (especially lower carbalkoxy)
  Aminoacyl (amide)
  Amino
  Nitro
  Cyano
  Thioether
  Sulfoxy
  Sulfone
  Sulfonic acid (and derivatives thereof)

In general, no more than about three such substituent groups, and usually no more than one, will be present for each 10 carbon atoms in the radical.

Usually, the nitrile used for preparing the amidoalkanesulfonic acid is a hydrocarbon mononitrile or dinitrile having up to about 12 carbon atoms. A particular preference is expressed for lower alkyl or lower alkenyl mononitriles (the word "lower" denoting radicals containing up to seven carbon atoms) such as acetonitrile, acrylonitrile and methacrylonitrile, especially the latter two.

The olefin is generally one having up to about 25 carbon atoms, with those having less than 10 carbon atoms being preferred. The olefin may be an aryl-substituted one such as styrene or t-butylstyrene or a terpene such as dipentene, but is usually aliphatic. Propene and the butenes, especially isobutene, are especially suitable. Substituted olefins (the word "substituted" being defined hereinabove) are equivalent to the corresponding unsubstituted ones for the purpose of this invention.

The fuming sulfuric acid is usually at least about 5% oleum and preferably about 20–50%; "5% oleum" refers to solutions consisting of 5% free sulfur trioxide and 95% $H_2SO_4$. Other solutions are similarly defined; e.g., "40% oleum" consists of 40% $SO_3$ and 60% $H_2SO_4$.

In calculating the oleum concentration, the amount of water contained in the other reagents is taken into consideration. For example, a commercially available nitrile (e.g., acrylonitrile) which contains some water is frequently used. This water will naturally decrease the free sulfur trioxide concentration of the oleum.

When the amidoalkanesulfonic acid is prepared in situ, the nitrile, olefin and fuming sulfuric acid are brought into contact. Preferably, the nitrile and fuming sulfuric acid are mixed no later than the time of addition of the olefin. Thus, the olefin is prevented from coming into contact with fuming sulfuric acid alone. For this purpose, all three reagents may be introduced into the reaction system simultaneously or the nitrile may be premixed with the fuming sulfuric acid, or a portion thereof as described hereinafter, and the olefin subsequently added. Depending on the efficiency of the reaction equipment, the mixing time of the nitrile and fuming sulfuric acid may be as little as one second or one minute, when such mixing time is necessary at all. It may, however, be longer in certain instances.

The relative proportions of nitrile to the other reagents is not critical. It is preferred to use at least one equivalent of nitrile per equivalent of olefin. (The term "equivalent" as used herein is a number of parts by weight equal to the equivalent weight of the compound, which is its molecular weight divided by the number of reactive sites therein. Thus, the equivalent weight of a monoolefin or mononitrile is equal to its molecular weight; that of a diolefin or dinitrile is half its molecular weight; and so on.) Usually, it is further preferred that the reagents previously recited be the only substances present in substantial quantities; that is, the only ones present except for inevitable impurities. In such instances, it is desirable to use a large excess of nitrile (for example, a mole ratio of nitrile to olefin from about 10:1 to about 40:1) whereupon the excess serves as a diluent for the reaction. However, it is also within the scope of this invention to use inert diluents such as ethers or chlorinated hydrocarbons. Typical examples of suitable diluents are 1,2-dichloroethane, carbon tetrachloride, ethylene glycol dimethyl ether and diethylene glycol dimethyl ether.

It is frequently desirable, though not essential, to carry out the reaction in an inert atmosphere such as nitrogen, helium, argon or the like.

The reaction temperature is generally between $-80°C$. and about $75°C$. The temperature of the mixture of the nitrile and fuming sulfuric acid is ordinarily maintained below $0°C$., preferably between about $-20°C$. and $-65°C$., prior to the addition of the olefin. When the olefin is a very volatile one such as propene, it is often beneficial to maintain the temperature below about $0°C$. during the entire addition period. The same is frequently true of less volatile olefins such as styrene, substituted styrenes and diisobutene. However, if a lower aliphatic olefin which is not as volatile as propene, such as isobutene, is used, it is preferred to add the greater part thereof (at least about 80% by weight thereof) to a nitrile-fuming sulfuric acid mixture which is maintained at about $10°–30°C$. After the olefin addition is complete, the reaction mixture is usually agitated at about $0°–30°C$. for a period of time long enough for the reaction to go to substantial completion.

The olefin may be added over a period as short as 5 minutes or as long as one hour or even more, the only important feature being control of the exothermic reaction which takes place during said addition. Since the reaction temperature is generally below about $30°C$., control of the reaction temperature may best be effected at least partly by controlling the rate of olefin addition.

From the standpoint of amidoalkanesulfonic acid production, the relative proportions of olefin and fuming sulfuric acid are not critical so long as at least enough sulfur and enough of the elements of water are present in the sulfuric acid to produce the desired amount of amidoalkanesulfonic acid. For the purposes of this invention, however, it is usually preferred that the reaction mixture be substantially homogenous at the time the organic hydroxy compound is added. When the amidoalkanesulfonic acid is produced in situ, homogeneity is conveniently maintained by employing a ratio of gram-atoms of combined sulfur in the fuming sulfuric acid to equivalents of olefin of at least about 4:1, preferably between about 4:1 and 7:1, and a ratio of moles of free sulfur trioxide to equivalents of olefin between about 1.5:1 and 3:1. If less fuming sulfuric acid or sulfur trioxide than this is used, the amidoalkanesulfonic acid frequently precipitates from the reaction mixture prior to formation of the ester.

According to this invention, the amidoalkanesulfonic acid ester is produced by contacting the acid with sulfur trioxide and then with an organic hydroxy compound. The sulfur trioxide may be employed in any one of several forms. For example, it may be employed as free sulfur trioxide or as a solution or dispersion thereof in a suitable diluent which is inert to the reagents used in the process. Alternatively, it may be employed in the form of oleum or fuming sulfuric acid. In a preferred embodiment, the sulfur trioxide is furnished by oleum which has been used in the in situ preparation of the amidoalkanesulfonic acid as described hereinabove.

When the amidoalkanesulfonic acid is solid at the time of contact with the sulfur trioxide, it usually interacts with the sulfur trioxide to form a liquid mass. This is true whether the sulfur trioxide is added in free form or as oleum. The temperature at which the two reagents come into contact is not critical; temperatures between about $-10°C$. and about $50°C$. are suitable, and about $0°–25°C$. is preferred. Generally, about 1–4 moles of sulfur trioxide is used per equivalent of amidoalkanesulfonic acid.

The amidoalkanesulfonic acid-sulfur trioxide mixture is then reacted with an organic hydroxy compound of the formula ROH, wherein R is a hydrocarbon or substituted hydrocarbon radical as previously defined. That is, the organic hydroxy compound is an alcohol or phenol. Usually, it is an alcohol and preferably an alkanol (that is, R is usually an aliphatic and preferably an alkyl radical). Lower alkanols (the word "lower" being defined hereinabove), most often methanol or ethanol, are especially preferred.

The amount of organic hydroxy compound used is not critical, although obviously that reagent will ordinarily be used in at least an equimolar amount with respect to the amidoalkanesulfonic acid in order that quantitative conversion to the ester is at least theoretically possible. More often, the organic hydroxy compound is used in excess, typically about 3–10 moles per mole of amidoalkanesulfonic acid.

The means by which the acid-sulfur trioxide reaction mass is contacted with the organic hydroxy compound is not critical; said reaction mass may be added to the hydroxy compound, or the reverse mode of addition may be used. Likewise, either may be added incrementally or continuously. The temperature during the second step is usually about 0°–50°C., preferably about 10°–30°C.

The contact time between the acid-sulfur trioxide reaction mass and the organic hydroxy compound need not be extremely long; usually about one hour or even less is sufficient. When the reaction is complete, the desired ester is isolated by conventional techniques.

The method of this invention is particularly adapted for use in continuous systems. It is frequently convenient to prepare the amidoalkanesulfonic acid continuously in situ and then to add the organic hydroxy compound at a later point in the continuous system.

The method of this invention is illustrated by the following examples.

EXAMPLE 1

A laboratory-scale continuous system is prepared by connecting three round-bottomed flasks, each fitted with a stirrer and the necessary inlet and outlet tubes, in series. The first flask contains inlets for acrylonitrile and oleum and an outlet at the bottom. The second contains an olefin inlet adapted for gas introduction and an overflow outlet at approximately the half-full level. The third contains an inlet for methanol.

Acrylonitrile (containing about 0.05% water) and 40% oleum are added to the first flask at rates of 29.2 grams and 3.39 grams per minute, respectively. The total amounts added are 1840 grams (34.8 moles) of acrylonitrile and 212.8 grams (2.37 gram-atoms of sulfur) of oleum. The temperature of the first flask is maintained at −40°C. by cooling in a Dry Ice bath.

The liquid is drained from the first to the second flask at a rate to provide a liquid volume of 50–100 ml. in the first flask. Isobutene, 56 grams (1 equivalent), is added to the second flask, above the surface of the liquid, at the rate of 0.89 gram per minute and is absorbed by the liquid in the flask as rapidly as it is added. The temperature of the second flask is maintained at 15°–20°C. by cooling in a water bath.

The liquid in the second flask is splashed into the third flask by vigorous stirring, and 96 grams (3 moles) of methanol is added to the third flask over 2 minutes at 5°C. The mixture is allowed to warm to room temperature and is then filtered; the residue is washed with acrylonitrile and the combined filtrate and washings are poured over 1000 grams of ice. The aqueous layer is separated and extracted with benzene and the combined extracts and organic layer are concentrated and dried over magnesium sulfate. Upon removal of volatile materials by vacuum stripping, a solid is obtained which is the desired methyl 2-acrylamido-2-methylpropanesulfonate. To the solid is added over 0.1 gram of p-methoxyphenol as a polymerization inhibitor.

EXAMPLE 2

Following substantially the procedure of Example 1, a reaction mixture is prepared from 400.3 grams (4.45 gramatoms of sulfur) of 40% oleum, 1930 grams (36.4 moles) of acrylonitrile (containing 0.013% water) and 56 grams (1 equivalent) of isobutene. The addition rates are the same as in Example 1 except that the oleum addition rate is 6.8 grams per minute. Following the completion of the acrylonitrile and isobutene addition, oleum addition is continued until the indicated amount has been introduced. The reaction mixture is then poured into 128 grams (4 moles) of methanol at 5°–10°C., over one hour. p-Methoxyphenol, 0.5 gram, is added as a polymerization inhibitor and the solution is poured over 1000 grams of ice. The organic layer is separated; the aqueous layer is washed with aqueous sodium sulfate solution and extracted with three 500-ml. portions of chloroform. The organic layer and chloroform extracts are dried over magnesium sulfate and the volatile materials are stripped to yield the desired methyl 2-acrylamido-2-methylpropanesulfonate which is recrystallized from a benzene-cyclohexane mixture. The recrystallized product melts at 78°–81°C.

EXAMPLE 3

Following substantially the procedure of Example 1, a reaction is carried out between 1142 grams (12.8 gramatoms of sulfur) of 42% oleum, 2235 grams (92.4 moles) of acrylonitrile (containing 0.159% water) and 168 grams (3 equivalents) of isobutene. The isobutene is added below the surface of the liquid in the second flask. Methanol is added continuously to the third flask as the reaction mass passes into it from the second flask; the total methanol used is 192 grams (6 moles). The final mixture is poured over ice and the organic layer is separated; the aqueous layer is extracted with a benzene-acrylonitrile mixture and the organic layer and extracts are washed with saturated sodium sulfate solution and stripped, yielding the desired methyl 2-acrylamido-2-methylpropanesulfonate which is recrystallized from toluene.

EXAMPLE 4

A laboratory-scale continuous system is prepared by connecting four round-bottomed flasks, each fitted with a stirrer and the necessary inlet and outlet tubes, in series. The first three flasks are connected as in Example 1; the third flask drains via a bottom outlet into the fourth.

Acrylonitrile (containing 0.159% water) and 42% oleum are introduced into the first flask at the rates of 19.4 grams and 6.64 grams per minute, respectively; the total amounts used are 1504.5 grams (16.79 gramatoms of sulfur) of oleum and 4450 grams (84 moles) of acrylonitrile. The first flask is maintained at −50°C. Isobutene is added to the second flask under the surface of the liquid, at 0.985 grams per minute; a total of 224 grams (4 equivalents) of isobutene is added. The reaction mass passes into the third flask and is splashed from there into the fourth by vigorous stirring; the fourth flask initially contains 192 grams of methanol and three additional portions of 192 grams (total 768 grams, 24 moles) are added as proportionate amounts of the reaction mass from the third flask pass into the fourth. The methyl 2-acrylamido-2-methylpropanesulfonate is recovered as described in Example 3.

EXAMPLE 5

Following the procedure of Example 4, methyl 2-acrylamido-2-methylpropanesulfonate is prepared from 1507.2 grams (16.7 gram-atoms of sulfur) of 38% oleum, 4450 grams (84 moles) of acrylonitrile containing 0.159% water, 224 grams (4 equivalents) of isobutene and 512 grams (16 moles) of methanol. The methanol is added to the fourth flask in four 128-gram portions.

EXAMPLE 6

A laboratory-scale continuous system is prepared by connecting five round-bottomed flasks, each fitted with a stirrer and the necessary inlet and outlet tubes, in series. The first three flasks are connected as described in Example 1. The third flask drains into the fourth via a U-tube so that the liquid volume in the third flask remains at 150–200 ml., and the fourth flask is connected via an overflow tube, at approximately the half-full point, to the fifth. Following substantially the procedure of Example 3, a reaction mass is prepared from 1671 grams (18.7 gram-atoms of sulfur) of 42% oleum, 4600 grams (86.9 moles) of acrylonitrile containing 0.159% water, and 224 grams (4 equivalents) of isobutene. Methanol is added continuously to the fourth flask, to a total of 832 grams (26 moles), and the liquid is splashed by vigorous stirring from the fourth flask into the fifth, which is cooled in an ice bath. The product is recovered by pouring the reaction mixture into ice water, neutralizing with 30% ammonium hydroxide solution and then treating as described in Example 3.

EXAMPLE 7

Following substantially the procedure of Example 6, methyl 2-acrylamido-2-methylpropanesulfonate is prepared from 1657.7 grams (18.5 gram-atoms of sulfur) of 42% oleum, 4580 grams (86.5 moles) of acrylonitrile, 168 grams (3 equivalents) of isobutene and 864 grams (27 moles) of methanol.

EXAMPLE 8

Following substantially the procedure of Example 6, methyl 2-acetamido-2-methylpropanesulfonate is prepared by the reaction of acetonitrile, 42% oleum, isobutene and methanol in the same molar proportions.

EXAMPLE 9

Following substantially the procedure of Example 6, methyl 2-acrylamido-2-phenylpropanesulfonate is prepared by the reaction of acrylonitrile, 42% oleum, styrene and methanol in the same molar proportions.

EXAMPLE 10

Following substantially the procedure of Example 6, n-butyl 2-acrylamido-2-methylpropanesulfonate is prepared by the reaction of 342 grams (3.9 gram-atoms of sulfur) of 39% oleum, 770 grams (14.5 moles) of acrylonitrile, 56 grams (1 equivalent) of isobutene and 148 grams (2 moles) of n-butyl alcohol. The desired ester is obtained as a syrupy liquid.

EXAMPLE 11

A slurry of 104.7 grams (0.51 equivalent) of 2-acrylamido-2-methylpropanesulfonic acid in 429.3 grams of acrylonitrile, produced by the reaction of isobutene and fuming sulfuric acid with excess acrylonitrile, is cooled to 3°C. and 61.5 grams of sulfur trioxide (0.745 mole, taking into account the water in the acrylonitrile) is added over one hour at 3°–5°C. The mixture is agitated for 15 minutes at 10°C. after completion of the sulfur trioxide addition, and then 125 ml. (3.1 equivalents) of methanol is added all at once, while the mixture is cooled in ice. The reaction causes a temperature rise to 35°C. Stirring is continued and when the temperature of the mixture has cooled to 20°C., the mixture is poured over excess ice. Toluene, 200 ml., is added and the organic layer is washed with sodium sulfate solution. The washings are extracted with chloroform and the combined organic solutions are dried over magnesium sulfate and stripped of volatile materials. The desired methyl 2-acrylamido-2-methylpropanesulfonate is recovered and recrystallized from toluene.

EXAMPLE 12

A slurry of 98 grams (0.47 equivalent) of 2-acrylamido-2-methylpropanesulfonic acid in 402 grams of acrylonitrile, identical with the slurry used in Example 11, is cooled to 4°C. and 98 grams of 65% oleum is added over 45 minutes, followed by 39 grams of 15% oleum over 10 minutes. The reaction mixture is stirred during the addition and is cooled to below 10°C. by submerging the vessel in ice water. Methanol, 125 ml. (3.1 equivalents), is then added all at once with stirring and the temperature rises to 55°C. It is cooled to 15°C. and poured over ice. Toluene is added and the desired methyl 2-acrylamido-2-methylpropanesulfonate is purified and isolated as described in Example 11.

EXAMPLE 13

A 25-gram portion of 65% oleum (containing 0.203 mole of sulfur trioxide) is poured over 20 grams (0.097 equivalent) of 2-acrylamido-2-methylpropanesulfonic acid. The mixture warms as the acid dissolves in the oleum. The viscous mixture is stirred for 10 minutes and is then poured into 300 ml. (7.42 equivalents) of methanol, while the vessel containing the latter is cooled with ice. After the mixture becomes homogeneous it is stripped to about 100 ml. and extracted with chloroform. The chloroform extracts are combined and dried over sodium sulfate, and the desired methyl 2-acrylamido-2-methylpropanesulfonate is obtained upon stripping the chloroform.

Esters of amidoalkanesulfonic acids, as a class, may be used as latent sources of the corresponding acids (e.g., by reaction with an alcohol) and as alkylating agents.

Esters of polymerizable amidoalkanesulfonic acids, such as methyl 2-acrylamido-2-methylpropanesulfonate, may be polymerized under free-radical conditions, either alone or in the presence of other monomers. The term "polymer," as used herein, includes addition homopolymers, copolymers, terpolymers and other interpolymers.

Polymerization by the free-radical method may be effected in bulk, solution, suspension or emulsion, by contacting the monomer or monomers with a polymerization initiator either in the absence or presence of a diluent at a temperature of about 0°–200°C. Suitable initiators include benzoyl peroxide, tertiary butyl hydroperoxide, acetyl peroxide, hydrogen peroxide, azobisisobutyronitrile, persulfate-bisulfite, persulfate-sodium formaldehyde sulfoxylate, chlorate-sulfite and the like.

A large variety of polymerizable compounds can be used to form interpolymers with these sulfonic acid esters. They include (1) unsaturated monohydric alcohols and esters thereof, (2) unsaturated acids and esters thereof, (3) unsaturated polyhydric alcohols and esters thereof, (4) vinyl cyclic compounds, (5) unsaturated ethers, (6) unsaturated ketones, (7) unsaturated amides, (8) unsaturated aliphatic hydrocarbons, (9) unsaturated alkyl halides, (10) unsaturated acid anhydrides, (11) unsaturated acid chlorides, and (12) unsaturated nitriles. Specific illustrations of such compounds are:

1. Unsaturated alcohols and esters thereof; Allyl, methallyl, crotyl, 1-chloroallyl, 2-chloroallyl, cinnamyl, vinyl, methylvinyl, 1-phenallyl, butenyl alcohols, and esters of such alcohols with saturated acids such as acetic, propionic, butyric, valeric, caproic and stearic; with unsaturated acids such as acrylic, alphasubstituted acrylic (including alkylacrylic, e.g., methacrylic, ethylacrylic, propylacrylic, etc., and arylacrylic such as phenylacrylic), crotonic, oleic, linoleic and linolenic; with polybasic acids such as oxalic, malonic, succinic, glutaric, adipic, pimelic, suberic, azelaic and sebacic; with unsaturated polybasic acids such as maleic, fumaric, citraconic, mesaconic, itaconic, methylenemalonic, acetylenedicarboxylic and aconitic; and with aromatic acids, e.g., benzoic, phenylacetic, phthalic, terephthalic and benzoylphthalic acids.

2. Unsaturated acids (examples of which appear above) and esters thereof with saturated alcohols, such as methyl, ethyl, propyl, isopropyl, butyl, isobutyl, sec-butyl, tert-butyl, 2-ethylhexyl, cyclohexyl or behenyl alcohols.

3. Unsaturated polyhydric alcohols, e.g., butenediol, and esters thereof with saturated and unsaturated aliphatic and aromatic, monobasic and polybasic acids, examples of which appear above.

4. Vinyl cyclic compounds including styrene, o-, m-, p-chlorostyrenes, bromostyrenes, fluorostyrenes, methylstyrenes, ethylstyrenes and cyanostyrenes; di-, tri-, and tetra-chlorostyrenes, bromostyrenes, fluorostyrenes, methylstyrenes, ethylstyrenes, cyanostyrenes; vinylnaphthalene, vinylcyclohexane, divinylbenzene, trivinylbenzene, allylbenzene, and heterocycles such as vinylfuran, vinylpyridine, vinylbenzofuran, N-vinylcarbazole, N-vinylpyrrolidone and N-vinyloxazolidone.

5. Unsaturated ethers such as methyl vinyl ether, ethyl vinyl ether, cyclohexyl vinyl ether, octyl vinyl ether, diallyl ether, ethyl methallyl ether and allyl ethyl ether.

6. Unsaturated ketones, e.g., methyl vinyl ketone and ethyl vinyl ketone.

7. Unsaturated amides, such as acrylamide, methacrylamide, N-methylacrylamide, N-phenylacrylamide, N-allylacrylamide, N-methylolacrylamide, N-allylcaprolactam, diacetone acrylamide and hydroxymethylated diacetone acrylamide.

8. Unsaturated aliphatic hydrocarbons, for instance, ethylene, propylene, butenes, butadiene, isoprene, 2-chlorobutadiene and alpha-olefins in general.

9. Unsaturated alkyl halides, e.g., vinyl fluoride, vinyl chloride, vinyl bromide, vinylidene chloride, vinylidene bromide, allyl chloride and allyl bromide.

10. Unsaturated acid anhydrides, e.g., maleic, citraconic, itaconic, cis-4-cyclohexene-1,2-dicarboxylic and bicyclo(2.2.1)-5-heptene-2,3-dicarboxylic anhydrides.

11. Unsaturated acid halides such as cinnamoyl, acrylyl, methacrylyl, crotonyl, oleyl and fumaryl chlorides or bromides.

12. Unsaturated nitriles, e.g., acrylonitrile, methacrylonitrile and other substituted acrylonitriles.

The especially preferred polymers are the copolymers with acrylic monomers; that is, with acids such as acrylic and methacrylic acids and their esters, amides and nitriles. Copolymers with acrylonitrile are especially useful for the preparation of textile fibers because of their affinity for dyes.

The preparation of polymers of polymerizable esters of amido-substituted sulfonic acids is illustrated by the following examples.

EXAMPLE 14

A resin flask is charged with 100 ml. of a 0.0008 N sulfuric acid solution, flushed with nitrogen and heated to 50°C. There are then added simultaneously, with stirring, the following: (1) a mixture of 100 grams of acrylonitrile and 3.4 grams of methyl 2-acrylamido-2-methylpropanesulfonate, (2) a solution of 0.75 part of potassium persulfate in 100 ml. of water, (3) a solution of 2.1 parts of sodium metabisulfite in 100 ml. of water, and (4) 100 ml. of a 0.0024 N solution of sulfuric acid. The addition time for the four solutions is 55 minutes. After addition is complete, the flask is cooled in ice water and the contents are poured into 3 liters of water. The desired copolymer precipitates and is washed with water and dried in a vacuum over at 70°C. It is found to have excellent incorporation of Sevron Blue 2G dye.

EXAMPLE 15

Following substantially the procedure of Example 14, a copolymer is prepared from 100 parts of acrylonitrile and 3.4 parts of methyl 2-acrylamido-2-phenylpropanesulfonate.

EXAMPLE 16

A mixture of 47.5 parts of styrene, 2.5 parts of methyl 2-acrylamido-2-methylpropanesulfonate and 0.1 part of azobisisobutyronitrile is heated overnight at 100°C., under nitrogen. During this time, the mixture solidifies. It is dissolved in benzene and reprecipitated by pouring into methanol. The precipitate is then filtered, washed with methanol and dried; it is the desired copolymer.

EXAMPLE 17

A mixture of 209.9 parts of isodecyl acrylate, 11.05 parts of methyl 2-acrylamido-2-methylpropanesulfonate and 331 parts of heptane is heated to 60°C. under nitrogen, with stirring. Azobisisobutyronitrile, 0.44 part, is then added and stirring is continued at 60°C. for 20 hours, yielding a heptane solution of the desired copolymer.

What is claimed is:

1. A method for the preparation of an ester of an amidoalkanesulfonic acid which comprises bringing into contact, at a temperature between about −10° and 50°C., said acid and sulfur trioxide as fuming sulfuric acid or as a solution or dispersion in a diluent which is inert to the reagents used, and subsequently contacting the reaction mass thus obtained, at a temperature of about 0°–50°C., with an organic hydroxy compound of the formula ROH, wherein R is a hydrocarbon or substituted hydrocarbon radical; with the proviso that the substituents on said substituted radical do not alter significantly its character or reactivity, and no more than about three such substituents are present for each 10 carbon atoms in the radical.

2. A method according to claim 1 wherein R is an alkyl radical.

3. A method according to claim 2 wherein the sulfur trioxide is furnished by fuming sulfuric acid.

4. A method according to claim 3 wherein the amidoalkanesulfonic acid is 2-acrylamido-2-methylpropanesulfonic acid.

5. A method according to claim 3 wherein the amidoalkanesulfonic acid is prepared in situ by the reaction of a hydrocarbon mononitrile or dinitrile having up to about 12 carbon atoms, an olefinic hydrocarbon having up to about 25 carbon atoms, and fuming sulfuric acid.

6. A method according to claim 5 wherein the sulfur trioxide used in the esterification reaction is furnished by the fuming sulfuric acid used in the preparation of the amidoalkanesulfonic acid.

7. A method according to claim 6 wherein the fuming sulfuric acid is at least 5% oleum.

8. A method according to claim 7 wherein about 1–4 moles of sulfur trioxide is used per equivalent of amidoalkanesulfonic acid during the esterification reaction.

9. A method according to claim 8 wherein R is a lower alkyl radical.

10. A method according to claim 9 wherein the amidoalkanesulfonic acid is prepared from a lower alkyl or lower alkenyl mononitrile and an aliphatic olefin having less than 10 carbon atoms.

11. A method according to claim 10 wherein the amidoalkanesulfonic acid is 2-acrylamido-2-methylpropanesulfonic acid, prepared from acrylonitrile and isobutene.

12. A method according to claim 10 wherein R is methyl.

13. A method according to claim 12 wherein the amidoalkanesulfonic acid is 2-acrylamido-2-methylpropanesulfonic acid, prepared from acrylonitrile and isobutene.

* * * * *